United States Patent
Lambov (10) Patent No.: US 11,899,641 B2
(45) Date of Patent: *Feb. 13, 2024

(54) TRIE-BASED INDICES FOR DATABASES

(71) Applicant: DataStax, Inc., Santa Clara, CA (US)

(72) Inventor: Branimir Zdravkov Lambov, Nesebar (BG)

(73) Assignee: DataStax, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/549,570

(22) Filed: Dec. 13, 2021

(65) Prior Publication Data
US 2022/0255014 A1 Aug. 11, 2022
US 2023/0006144 A9 Jan. 5, 2023

Related U.S. Application Data

(63) Continuation of application No. 16/020,936, filed on Jun. 27, 2018, now Pat. No. 11,204,905.

(51) Int. Cl.
*G06F 16/22* (2019.01)
*C07D 209/86* (2006.01)
*H10K 85/60* (2023.01)
*H10K 50/15* (2023.01)
*H10K 50/17* (2023.01)

(52) U.S. Cl.
CPC ....... *G06F 16/2246* (2019.01); *C07D 209/86* (2013.01); *G06F 16/2255* (2019.01); *H10K 85/624* (2023.02); *H10K 85/626* (2023.02); *H10K 85/6572* (2023.02); *H10K 50/15* (2023.02); *H10K 50/17* (2023.02)

(58) Field of Classification Search
USPC ......................................... 707/747, 797, 830
See application file for complete search history.

(56) References Cited

U.S. PATENT DOCUMENTS 5,721,899 A * 2/1998 Namba ............... G06F 16/322
707/999.005
6,175,835 B1 * 1/2001 Shadmon ............ G06F 16/2246
707/696

(Continued)

OTHER PUBLICATIONS

United States Office Action, U.S. Appl. No. 16/020,936, filed Jun. 10, 2020, 11 pages.

(Continued)

*Primary Examiner* — Cam Linh T Nguyen
(74) *Attorney, Agent, or Firm* — Fenwick & West LLP (57) ABSTRACT

A database system uses byte ordering for keys and a trie index to reference stored data. The keys of a database are converted into byte-comparable sequences of byte values. The trie index is generated including nodes connected by edges defining paths from a root node to leaf nodes. Each edge is associated with at least one byte value such that each path from the root node to a leaf node through one or more edges defines a unique byte prefix for a byte-comparable sequence of byte values. The leaf node of each path is associated with a database location value. A record is accessed in the database using a database location value determined from referencing the trie index using a byte-comparable sequence of byte values of the record generated from a key of the record. A trie structure and byte ordered keys may be used for partition or row indices.

20 Claims, 9 Drawing Sheets

(56) References Cited

U.S. PATENT DOCUMENTS

| | | | |
|---|---|---|---|
| 6,208,993 B1* | 3/2001 | Shadmon | G06F 16/30 707/999.102 |
| 6,505,206 B1* | 1/2003 | Tikkanen | G06F 16/9027 707/812 |
| 6,560,610 B1* | 5/2003 | Eatherton | H04L 45/742 707/999.102 |
| 6,691,171 B1* | 2/2004 | Liao | H04L 45/74591 709/245 |
| 7,111,071 B1* | 9/2006 | Hooper | H04L 45/74591 370/395.32 |
| 7,249,149 B1* | 7/2007 | Eatherton | H04L 45/74591 707/999.102 |
| 7,376,657 B1* | 5/2008 | Mehta | H04L 45/74591 707/693 |
| 7,620,640 B2* | 11/2009 | Sample | G06F 16/322 |
| 7,933,885 B1* | 4/2011 | Lambiri | G06F 7/02 707/706 |
| 9,537,972 B1* | 1/2017 | Edwards | H04L 43/106 |
| 2003/0200211 A1* | 10/2003 | Tada | G06F 16/93 707/999.005 |
| 2003/0204513 A1* | 10/2003 | Bumbulis | G06F 16/2246 |
| 2005/0027679 A1* | 2/2005 | Sample | G06F 16/322 |
| 2005/0114298 A1* | 5/2005 | Fan | G06F 16/2474 |
| 2006/0083247 A1* | 4/2006 | Mehta | H04L 45/60 370/395.32 |
| 2015/0310165 A1* | 10/2015 | Mann | G16B 30/10 506/2 |
| 2015/0324485 A1* | 11/2015 | Tsirkin | G06F 16/9027 707/769 |
| 2016/0092483 A1* | 3/2016 | Raja | G06F 16/2246 707/745 |
| 2016/0371376 A1* | 12/2016 | Hassan | G06N 20/00 |
| 2017/0109399 A1* | 4/2017 | Stearn | G06N 5/04 |
| 2018/0212876 A1* | 7/2018 | Bacthu | H04L 45/748 |
| 2018/0324096 A1* | 11/2018 | Moore | H04L 45/48 |

OTHER PUBLICATIONS

United States Office Action, U.S. Appl. No. 16/020,936, filed Nov. 19, 2020, 12 pages.

United States Office Action, U.S. Appl. No. 16/020,936, filed Apr. 6, 2021, 11 pages.

* cited by examiner

Convert keys of a database into byte-comparable sequences of byte values
405

Generate a trie index for the database mapping unique byte prefixes of the byte-comparable sequences of byte values to database location values
410

Store the trie index
415

Convert a partition key for a record into a first byte-comparable sequence of bytes and a clustering key for the record into a second byte-comparable sequence of bytes
705

Reference a trie partition index using the first byte-comparable sequence of bytes to determine a partition for the record
710

Reference a trie row index of the partition using the second byte-comparable sequence of bytes to access the record from the database
715

TRIE-BASED INDICES FOR DATABASES

CROSS REFERENCE TO RELATED APPLICATIONS

This application is a continuation of co-pending U.S. application Ser. No. 16/020,936, filed Jun. 27, 2018, allowed, which is herein incorporated in its entirety by reference.

BACKGROUND

The disclosure generally relates to managing databases, and in particular to database indexing using trie-based indices.

Database systems such as Cassandra have a heavy reliance on comparisons. Comparisons are used throughout read and write paths, coordination, compaction, etc. to be able to order and merge results. Comparisons also supports a range of data types which often require the compared object to be completely in memory to order correctly, which in turn has necessitated interfaces where comparisons can only be applied if the compared objects are completely loaded.

This has some negative implications on the performance of the database, both in terms of the time it takes to load, compare and garbage collect, as well as in terms of the space required to hold complete keys in on-disk indices and deserialized versions in in-memory data structures. Furthermore, the reliance on comparisons forces Cassandra to use only comparison-based structures, which can be inefficient.

SUMMARY

Embodiments relate to using byte ordering for keys and a trie index for referencing a database. In some embodiments, keys of a database are converted into byte-comparable sequences of byte values. A trie index for the database is generated including nodes connected by edges defining paths from a root node to leaf nodes, each edge being associated with at least one byte value such that each path from the root node to a leaf node through one or more edges defines a unique byte prefix for a byte-comparable sequence of byte values, the leaf node of each path being associated with a database location value. To access a record, a key for the record is converted into a byte comparable sequence of byte values. The trie index is referenced using the byte-comparable sequence of byte values to determine a database location value of the record. The record is accessed using the database location value of the record.

Some embodiments include a system including a database and processing circuitry. The processing circuitry converts keys of the database into byte-comparable sequences of byte values, and generates a trie index for the database. The trie index includes nodes connected by edges defining paths from a root node to leaf nodes. Each edge is associated with at least one byte value such that each path from the root node to a leaf node through one or more edges defines a unique byte prefix for a byte-comparable sequence of byte values. The leaf node of each path is associated with a database location value. The processing circuitry converts a key for a record into a byte-comparable sequence of byte values, references the trie index using the byte-comparable sequence of byte values of the record generated from the key to determine a database location value of the record, and accesses the record in the database using the database location value of the record.

Some embodiments include a non-transitory computer readable medium storing instructions that when executed by a processor causes the processor to: convert keys of the database into byte-comparable sequences of byte values; generate a trie index for the database, the trie index including nodes connected by edges defining paths from a root node to leaf nodes, each edge being associated with at least one byte value such that each path from the root node to a leaf node through one or more edges defines a unique byte prefix for a byte-comparable sequence of byte values, the leaf node of each path including a database location value; convert a key for a record into a byte-comparable sequence of byte values; reference the trie index using the byte-comparable sequence of byte values of the record generated from the key to determine a database location value of the record; and access the record in the database using the database location value of the record.

Other embodiments include components, devices, systems, improvements, methods, processes, applications, computer readable mediums, and other technologies related to any of the above.

DETAILED DESCRIPTION

Embodiments relate to applying byte ordering and trie indices to database systems. Examples of database systems may include, but are not limited to, Cassandra, DynamoDB, CosmosDB, Spanner, etc. The comparing and ordering of objects in database systems such as Cassandra is improved by byte ordering for data types used in keys. The terms "byte order" or "byte-comparable" refers to the property of being ordered via lexicographic compare on the unsigned values of the byte contents. Some of the data types in Cassandra are byte ordered (e.g. strings, blobs), but other heavily used ones (e.g. integers, uuids) are not byte ordered. As such, non-byte-comparable data types are converted to byte comparable data sequences of bytes and used to reference a trie index.

The universal availability of byte ordering for all data types used for keys provides various advantages. Comparisons can be done using a single process, and core machinery for data access does not need to know how to handle the individual data types. Prefix differences are enough to define order; unique prefixes can be used instead of complete keys. Tries can be used to store, query and iterate over sets of keys, providing fast lookup and prefix compression. Merging can be performed by merging tries, significantly reducing the number of necessary comparisons.

The trie index includes nodes connected by edges, with each edge being associated with one or more byte values. Each path from a root node to a leaf node through one or more edges defines a unique byte prefix for a byte-comparable sequence of byte values. A database location value is stored at each leaf node. As such, the trie index provides a mapping of keys as represented by byte-ordered sequences of byte values to database location values. In some embodiments, a database is referenced using a trie based partition index and a trie based row index.

Example Database System

Figure 1:
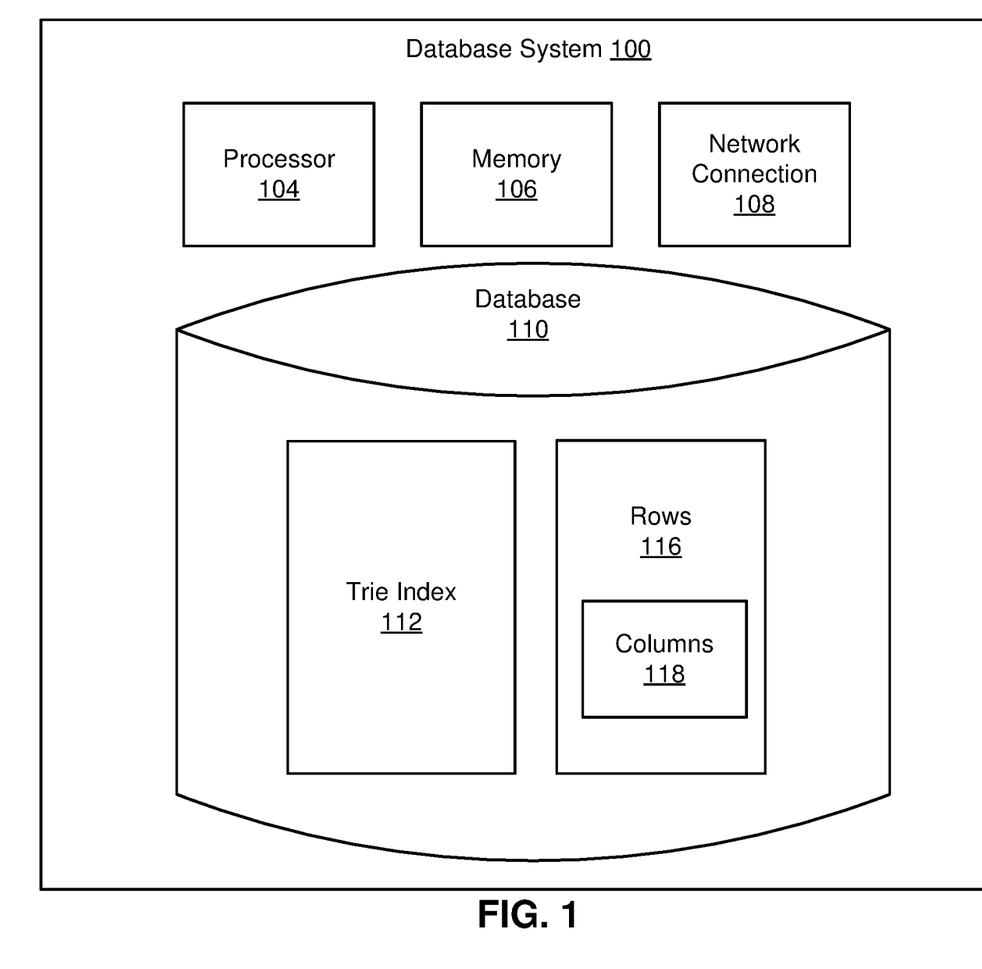
FIG. 1 is a schematic block diagram of a database system, in accordance with some embodiments.

FIG. 1 is a schematic block diagram of a database system 100, in accordance with some embodiments. The database system 100 includes a processor 104, a memory 106, a network connection 108, and a database 110. The memory 106 stores instructions that when executed by the processor 104, causes the processor 104 to control operation of the database system 100. For example, the processor 104 may service requests and manage the database 110. The processor 104 may also update the database 110 by managing the trie index 112, and reading and writing data files to the database 110. The network connection 108 connects the database system 100 to a network, which may include the Internet.

The database 110 includes a trie index 112 providing an index of records stored in rows 116 and columns 118 of the database 110. Each row 116 may include a record including data stored in columns 118 of the row 116. In some embodiments, the database 110 may include one or more trie indices 112 and partitions, with each trie index 112 being associated with a partition 114. The trie index 112 includes a trie data structure that describes a mapping between sequences of byte values and database location values of the partition 114. In some embodiments, the partition 114 is stored in one or more data files. Cassandra, for example, uses short string table (SSTable) data files to store partitions of a database. The database location value may indicate the position in a data file storing a row 116.

In some embodiments, the database 110 includes multiple rows 116 that operate as a main unit of data. To find a row, a primary key is used to reference the trie index 112. Here, the trie index 112 is also referred to as a primary trie index.

In embodiments where the database system 100 is part of a distributed database, such as Cassandra, there is an additional level of splitting where a database table may include multiple partitions 114, each partition 114 being a set of rows that are placed together on the same node (e.g., machine/server). To address in these distributed database systems, a partition may be referenced by one part of a primary key, referred to as a "partition key," and the individual row within a partition is addressed by the rest of the primary key, referred to as a "clustering key". As discussed in greater detail below in connection with FIG. 2, a partition key may be used to reference a partition trie index 212, and the clustering key may be used to reference a row trie index 220.

As such, a table contains a list of partitions split among the individual nodes of the cluster (where the partition key is used to select the individual partition and server), and each partition contains a list of rows (where the clustering key selects the individual row). The primary key is a combination of the primary and clustering keys.

The trie index 112 is referenced using byte-comparable sequences of byte values as keys. For example, to access data for read or write, a key is generated to query the trie index. The key may include different data having different data types. The key is converted into the byte-comparable sequence of byte values. The conversion may include converting the different data types used for the key into byte-comparable byte values. Accordingly, byte order is available for any data type used for keys. The byte-comparable sequence of byte values is then used to traverse the trie index 112 for a database location value. The trie index 112 and byte-comparable byte values are discussed in greater detail in connection with FIGS. 3A, 3B, 4, and 5.

Figure 2:
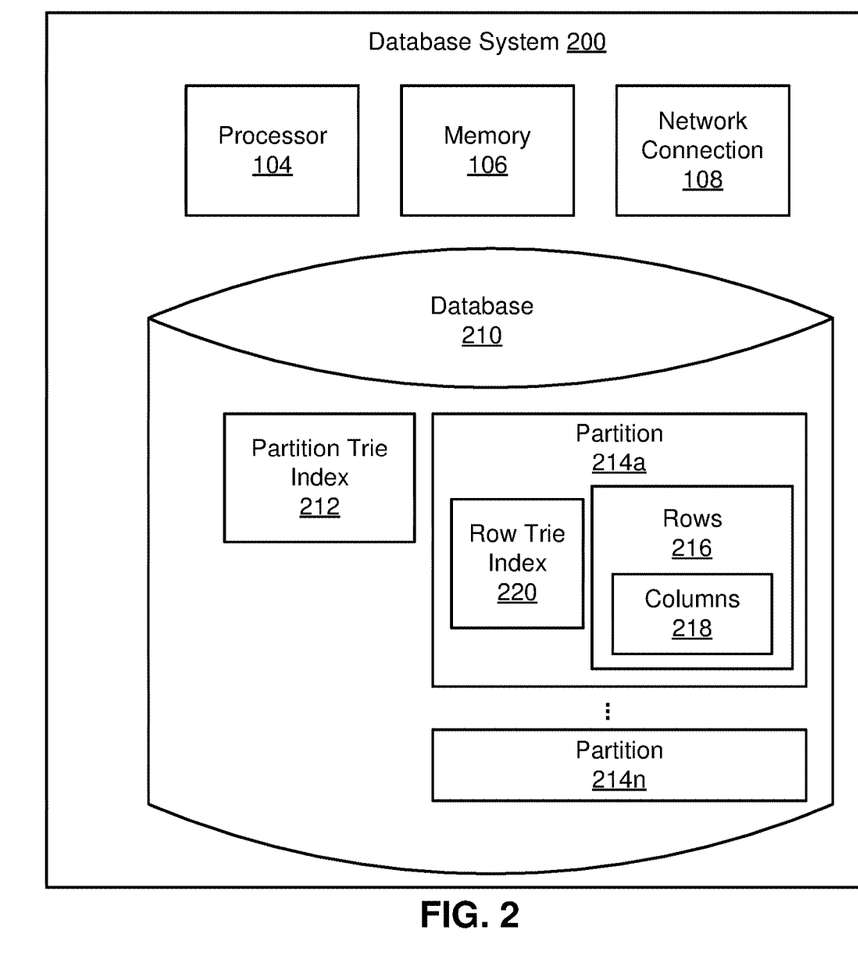
FIG. 2 is a schematic block diagram of another database system, in accordance with some embodiments.

FIG. 2 is a schematic block diagram of a database system 200, in accordance with some embodiments. The database system 200 includes a database 210 including multiple partitions 214a through 214n (each referred to as partition 214), and a partition trie index 212 of the partitions 214a through 214n. As shown for the partition 214a, each partition 214 may include a row trie index 220, rows 215, and columns 210.

The partition trie index 212 is an index that references multiple partition 214, and thus can be used to identify a partition and the row index 220 of the partition 214. Like the database system 100, the database system 200 includes a processor 104, a memory 106, and a network connection 108.

The database system 200 is a database node of a distributed database system, such as Cassandra. A table of the database 210 may be distributed across a cluster of database nodes, each database node including one or more partitions 214 of the distributed database, and with at least a portion of the partitions 214 including an associated row trie index 220 for the rows 216 of the partition 214. A database node may include multiple partitions 214. Each node may use the partition trie index 212 to identify a particular partition 214, including partitions stored in other nodes.

The partition trie index 212 and row trie index 220 provide an index of records stored in the rows 216 and columns 218 of the partition 214. The partition trie index 212 maps a specified partition key to particular partition 214 and the associated row trie index 220 for the partition 214. The row trie index 220 is used to iterate from a given clustering key in forward or reverse direction (where exact key lookup is just a special case) along the rows 116. The partition trie index 212 and row trie index 220 each includes a trie data structure that describes a mapping between sequences of byte values and database location values of the database 110. For example, the partition trie index 212 maps to database location values of the row trie indices 220, and each row trie index 220 maps to database location values of the rows. In some embodiments, each partition 214 may be stored in one or more data files. In some embodiments, a subset of the partitions 214 include a row trie index 220.

Byte Order Types

A database system may use non-byte-order-comparable data types (e.g., integers, uuids, etc.) for keys. For each data type, a conversion function can be defined that maps each possible value to a sequence of bytes, such that whenever two values are converted using this function, the result of lexicographically comparing the mappings is the same as the result of comparing the original values using the comparison function for the type.

To be able to completely abstract type information away from the storage machinery, lists of typed values (e.g., the individual components of a clustering key) are flattened into single byte sequences. It is possible to also define a mapping for reversed types within a list, e.g. by flipping all bits of the encoded byte sequence. Some example data types that may be converted to byte values include Fixed length unsigned integers (murmur token, date/time), fixed-length signed integers (byte, short, int, bigint), fixed-size floating-point numbers (float, double), multi-component sequences (partition or clustering keys, tuples), bounds and nulls, variable-length byte comparables (ASCII, UTF-8 strings, blobs, InetAddress), variable-length integers (varint, RandomPartitioner token), and variable-length floating-point decimals (decimal).

Tries

Figure 3A:
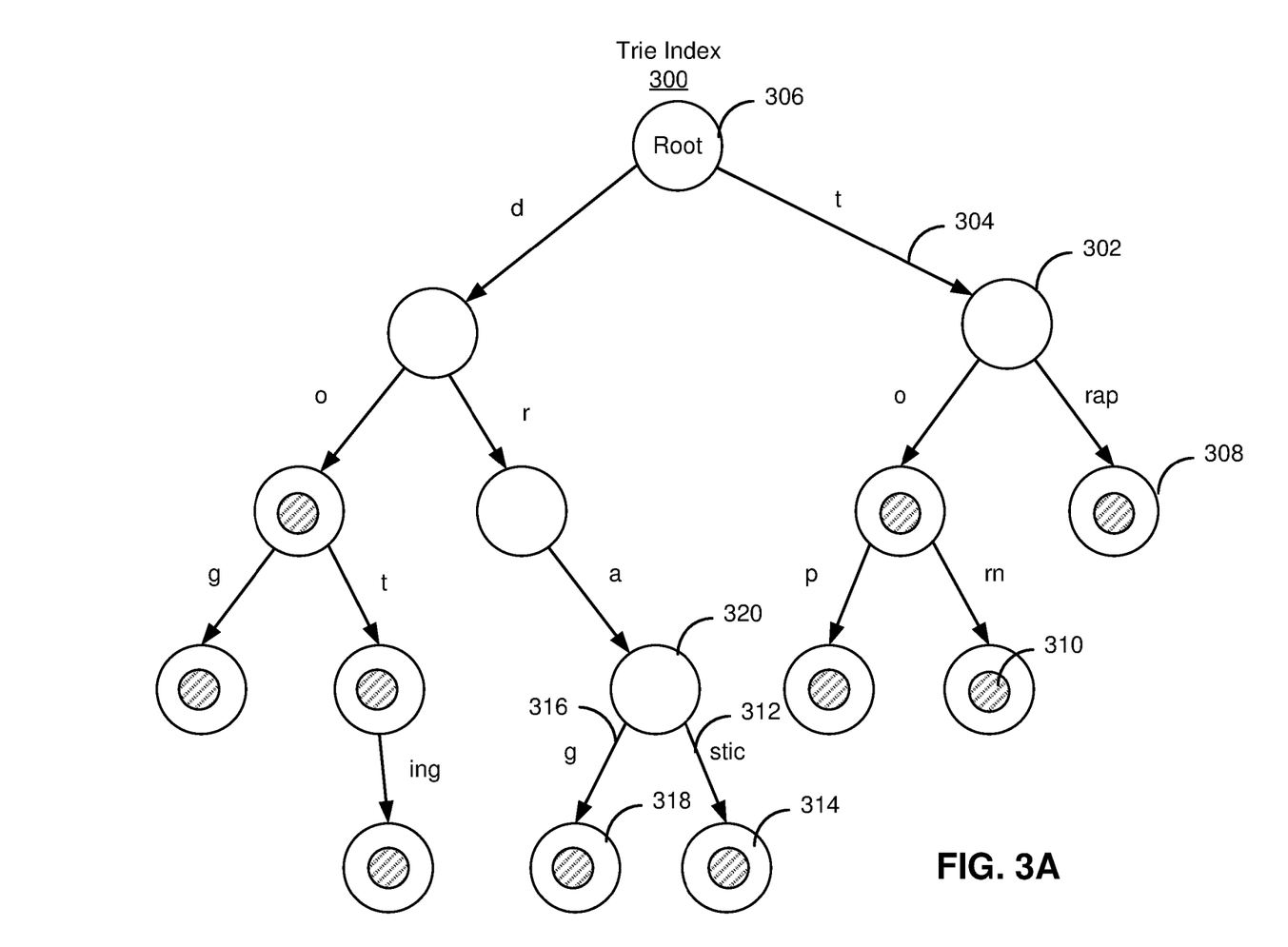
FIGS. 3A and 3B are examples of trie indices, in accordance with some embodiments.

A trie is a data structure that describes a mapping between sequences and associated values. A trie index refers to a trie that is used for mapping byte-comparable sequences (or their unique prefixes) to database location values. Mapping refers to the process of obtaining a database location value that corresponds to a particular key (e.g., mathematically, the result of applying a function). An "index," refers to a data structure that facilitates the mapping. "Indexing" refers to a process of creating the data structure. FIG. 3A is an example of a trie index 300, in accordance with some embodiments. The trie index 300 is an example of the trie index 112, the partition trie index 212, or the row trie index 220.

The trie index 300 includes nodes 302 connected by edges 304 defining paths from a root node 306 to leaf nodes 308. Each edge 304 is associated with a byte value such that each path from the root node 306 to a leaf node 308 through one or more edges 304 defines a unique byte prefix. In the example of FIG. 3, the byte prefixes are represented by letters of the alphabet. The root node 306 is connected to an edge associated with the byte value "d," and another edge associated with the byte value "t." The words formed by traversing the edges 304 are analogous to byte-comparable sequences of bytes of a key. The leaf node 308 of each path includes a database location value 310.

A valid word in the trie index 300 is encoded by a path starting from the root node 306 of the trie where each edge 304 is labeled with the next byte value of the sequence, and ending in the leaf node 308 which contains the "payload" 310 associated with the sequence of bytes.

This means that in a constructed trie index 300 finding the payload associated with a sequence of bytes is a matter of following the edges 304 (also called "transitions") from the root node 306, and along edges 304 labeled with the consecutive byte values (or characters, as represented in FIG. 3) of the word, and retrieving the payload 310 associated with the destination. For the example the partition trie index 212 and the row trie index 220, the sequence of byte values of the partition key is used to traverse the nodes of the partition trie index 212 to identify a partition and the associated row trie index 220 of the partition. The sequence of byte values of the clustering key is used to traverse the row trie index 220 to access the row within the partition. If the traversal destination does not result at a leaf node 308, or if at any point in the path there is no transition in the trie index 300 matching the byte value, the trie index 300 does not have an association for the byte sequence. Among other things, complexity is optimized because the complexity of lookup is thus O(len(sequence)) transitions, where the cost of taking a transition is usually constant.

From a storage space perspective, an advantage of a trie index 300 as a data structure for storing a map is to avoid storing of redundant prefixes. All byte-comparable sequences of bytes that start with the same sequence are stored as a representation of that sequence only once. If prefixes are commonly shared, this can save a great deal of space. For example, the byte values represented by the words "drag" and "drastic" share byte prefixes represented by the characters "dra."

When the items stored in the trie index 300 are lexicographically (=byte) ordered, the trie index 300 is an ordered structure. The trie index 300 can be walked in order and it is also possible to efficiently list the items between two given keys. A trie index 300 can be constructed from sorted input, incrementally storing the data directly to disk and building an efficient read-only on-disk data structure.

In some embodiments, trie index 300 is an ordered byte source to payload map that is applied to the indices of Cassandra. When writing to the index, each key is mapped into a byte-comparable sequence of bytes (also referred to as the byte ordered representation), and an on-disk trie of byte-ordered representations of keys mapping into positions in a data file is created.

For an exact match for a key, a byte-ordered representation of the key is generated and used to traverse the trie. If the match is found, the data file position is known. If there is no match, then there is no data associated with the key.

For a greater-than/greater-or-equal match for a key, the byte-ordered representation is used to create a path that leads to the first matching data position in the data file. The path is used to iterate the greater keys in the data file.

Unique Byte Prefixes

The trie index 300 is used to find a position in a data file for a given key. It needs to be able to find the correct position for any existing key, but there is no need for it to be exact on keys that are not present in the data file—since the data file contains a copy of the key at the start of each partition, we can simply check if the key we are searching for matches the key at the position returned by the index.

This allows us to use a simple optimization: instead of storing the full key in the trie index, we can store only a prefix of the key that is unique among all indexed values. This means intermediate nodes are in the trie only if a prefix is shared by multiple keys, which normally reduces the number of nodes and transitions in the trie to about twice the number of values. With reference to FIG. 3, the edge 312 to the leaf node 314 is associated with multiple byte values represented by "stic." The edge 316 to the leaf node 318 is associated with a single byte value represented by "g." The node 320 is an intermediate node shared by multiple keys and leaf nodes.

Use of unique byte prefixes in the trie index 300 rather than full byte-comparable sequences of bytes also reduces the number of edges 304 that must be traversed in the trie index 300 from the root node 305 to a leaf node 308. In a well-balanced key set (such as the one where the byte-ordered key starts with a hash token) the lookup complexity becomes O(log n) transitions Trie Index Storage Accessing information from non-volatile memory is usually performed in page units, where for every data access the complete disk page that contains the data is loaded. The trie index 300 may be stored across multiple disk pages. The trie index 300 may be many times larger than a disk page, and require thousands or millions of disk pages to store. The out-of-cache efficiency is low if a new disk page is read every time a new node is examined. The trie index 300 may be constructed in a "page-packed manner" to minimize traversal across different disk pages during lookup.

Figure 3B:
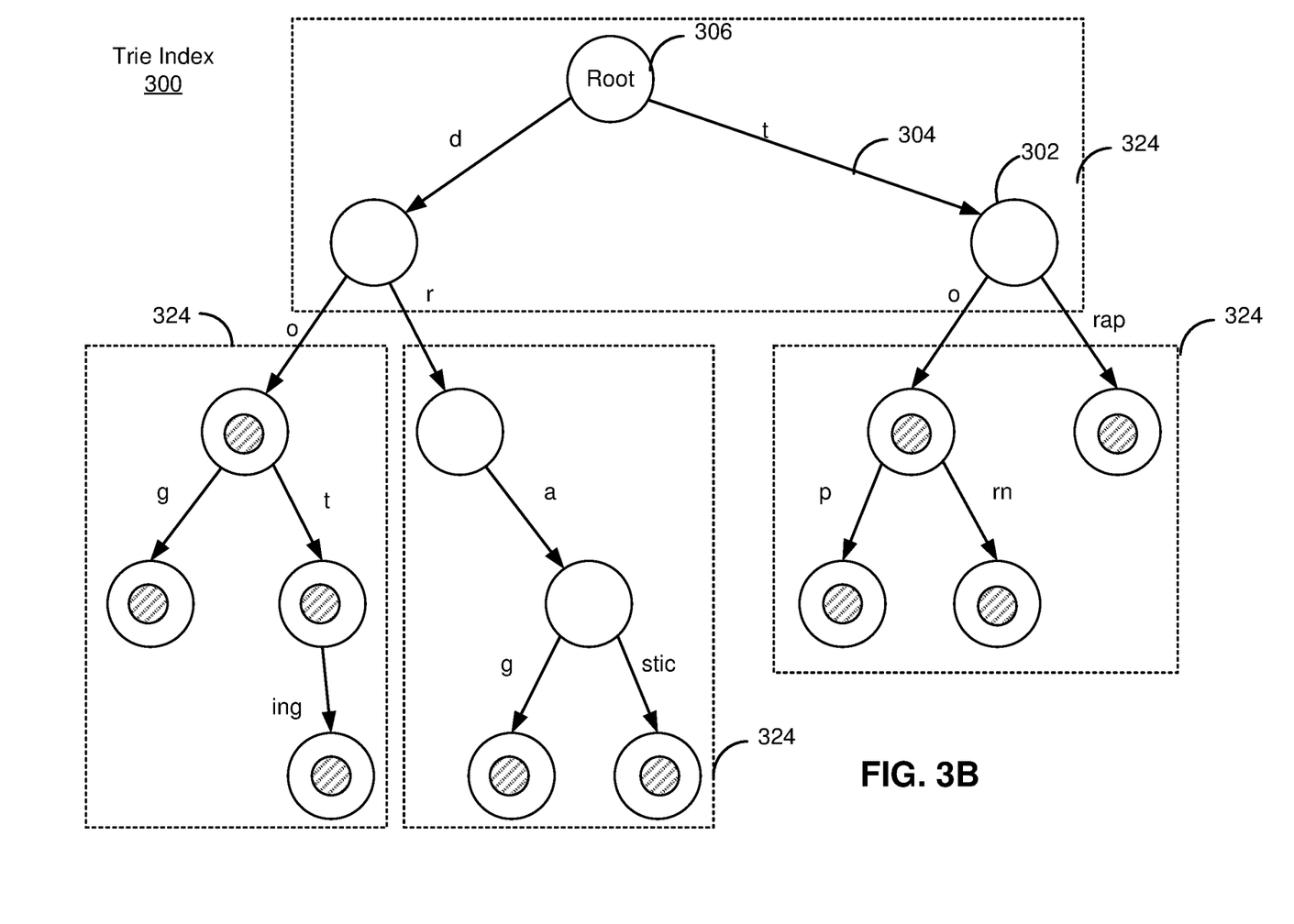

FIG. 3B shows the trie index 300 stored in a page-packed manner, in accordance with some embodiments. The trie index 300 is distributed across four disk pages 324. Wide sections of the trie index 300 may be packed in each disk page 324. As such, each time a disk page 324 is opened, several transitions between nodes 302 along edges 304 may be performed before leaving the disk page 324.

In some embodiments, the page-packed manner of storage is generated starting from the root node 306 and doing a breadth-first walk, placing the encountered nodes on a disk page 324 until the disk page 324 is filled. The target transitions of the encountered nodes from the breadth-first walk are placed in a queue, and the process is repeated to fill other disk pages 324.

In some embodiments, more suitable for database indexing because it can be done as part of an incremental construction process, is to do the packing from the bottom up—when the incremental construction algorithm completes a node 304 it is not immediately written to a disk page 304. Instead, the size of the branch rooted at this node is evaluated, and a node is written to disk only after the size of the branch rooted at its parent becomes larger than a page (or the data is exhausted). Performing this write reduces the size of the parent branch (as it can now refer to the positions of the children on disk) which from there on can be treated like a leaf, and the process can continue recursively until all data is exhausted.

The bottom-up process has a performance benefit over the top-down: with top-down the root page is full and leaf pages take combinations of unrelated smaller branches; with bottom-up the leaf pages take as much information as possible about a branch, while the root often remains unfilled. For the best possible out-of-cache efficiency we would prefer the set of non-leaf pages to be as small as possible. Having larger leaf page branches means more of the trie data is in the leaf branches and thus the size of that intermediate node set is smaller.

Trie Index Node Types

A trie index may be stored in memory, including volatile or non-volatile memory (e.g., a disk). To improve the efficiency of storing the information about the edge transitions in a node of a trie index, nodes of multiple types may be used. Node types can define the size of each pointer of the node, the number of children of the node in the trie index, or both.

To maintain that the size of the structure is proportional to the number of overall transitions, the node transitions need to be stored sparsely. Typically this is done using a list of transition characters and binary searching among them to make a transition.

This binary search is inefficient and it is preferable to avoid it as much as possible. To do this, and to save space, an on-disk trie index may use typed nodes. The node types may include: final with no transitions (PAYLOAD_ONLY); one transition (SINGLE), which has to store only the character and target for that transition; a binary-searched list of transitions (SPARSE), where the number of characters, each character and the targets are stored; or a consecutive range of transitions (DENSE), where the first and last character and targets are stored, possibly including some null transitions.

In a well-balanced and populated trie, the nodes where lookup spends most time (the nodes closest to the root) are DENSE nodes, where finding the target for the transition is a direct calculation from the code of the character. On the other hand, most of the nodes (the ones closest to the leaves) are PAYLOAD_ONLY, SINGLE or SPARSE to avoid taking any more space than necessary.

An objective for the trie storage format is to achieve the smallest possible packing (and thus smallest cache usage and disk reads), thus we choose the type that results in the smallest representation of the node. DENSE type gets chosen naturally when its encoding (which avoids storing the character list but may include null targets) is smaller than SPARSE. Nodes within a page may be of different types, and some nodes can be represented in more than one way: e.g. a node with "a" transition to X may be a SINGLE encoded as something like (SINGLE, "a", X), SPARSE encoded as (SPARSE, 1, "a", X), or DENSE encoded as (DENSE, "a", "a", X), where the first one will be chosen as the smallest; a node with "a" transition to X and "c" transition to Y can be (SPARSE, 2, "a", "c", X, Y) or (DENSE, "a", "c", X, null, Y) where the first is smallest, but a node with "a" transition to X and "b" transition to Y can be (SPARSE, 2, "a", "b", X, Y) or (DENSE, "a", "b", X, Y) where the dense one is smallest.

Pointer Sizes

Another optimization in the storage format of the trie index may be used because most nodes in the trie are in the lower levels of the tree and thus close to leaves. As such, the distance between the node and its target transitions when laid out during the construction process is small. As such, pointers are stored as distances and the node types are chosen to use the smallest size of integer which fits all its pointers.

This is even more true for a page-aware layout, where all internal transitions within the page (i.e. >99% of all transitions in the trie) can be stored using 12 bits or less.

This is heavily used via further specialization of the node types: e.g. there may be INPAGE_DENSE, DENSE_16 to DENSE_40 as well as DENSE_LONG subtypes which differ in the size of pointer they use.

Primary Index

In a distributed database system, the purpose of the primary index (e.g., of an sstable in Cassandra) is to be able to map a key containing a partition key and clustering key to a position in the sstable data file which holds the relevant row or the closest row with a greater key and enables iteration of rows from that point on. Partition keys are normally fully specified, while clustering keys are often given partially or via a comparison relation. They are also treated differently by all the infrastructure and conventionally have different index structures.

Partition Index

The purpose of a partition index is to map a specified partition key to a row index for the partition. A partition index also needs to support iteration from a (possibly partially specified) partition position. For example, the partition trie index 212 is a partition index that supports iteration from a (possibly partially specified) partition position.

In addition to wide partitions where a row index is mandatory, Cassandra is often used for tables where the partitions have only a couple of rows, including also ones where the partition key is the only component of a primary key, i.e. where row and partition are the same thing. For these situations it makes no sense to actually have a row trie index 220 and the partition trie index 212 should point directly to the data.

The application of tries to a partition index may include creating a trie mapping unique byte-ordered partition key prefixes to either: a position in a row index file which contains the row index of the rows within that partition, or a position in the data file containing the relevant partition (if a row index is not necessary). A single table can have both indexed and non-indexed rows.

Lookup in partition trie index 212 is accomplished by converting a partition key to its byte-ordered representation and following the transitions for its bytes. If at any point the trie does not offer a transition for the next byte but is not a leaf node, then the data file does not contain a mapping for the given key. If a leaf of the trie is reached, then the prefix of the partition key matches some content in the file, which may or may not be a full match for the partition key. The leaf node points to a place in the row trie index 220 or data file. In either case the first bytes at the specified position contain a serialization of the partition key, which we can compare to the key being mapped. If it matches, the partition is found. If not, since the stored prefixes are unique, no data for this partition exists in this data file.

In some embodiments the partition trie index 212 can also store a number of bits of the hash of the partition key, which can be used as a quick filter to reject non-matching keys with high probability without needing to refer to the data file or row index to fetch the complete key. For example, each leaf node of the trie index 212 may store hash bits. To access a record, a key for the record is converted into another byte-comparable sequence of bytes. The trie index 212 is traversed from the root node to a leaf node for a unique byte prefix of the byte-comparable sequence of bytes. The hash bits of the leaf node are compared to a remaining portion of the byte-comparable sequence of bytes to determine whether the record is stored in the database. In various embodiments, the hash bits of the leaf node may be compared to a hash value computed from the original key, a hash value computed from the remaining portion of the byte-comparable sequence of bytes, or a hash value computed from the whole of the byte-comparable sequence of bytes. Here, if the given key matched a prefix associated with the leaf node but not the hash bits, the key is determined as failing to match a record in the database and can be skipped without having to reference a row trie index 220 or data file of the partition identified by the leaf node. If the hash bits match the hash value, the probability that the key matches a record in the database is high.

Row Index

The row trie index 220 is a row index. Unlike the partition trie index 212, the row index is used to iterate from a given clustering key in forward or reverse direction (where exact key lookup is just a special case).

Rows are often very small (they could contain a single int or no columns at all) and thus there is a real possibility for the row indices to become bigger than the data they represent. This is not a desirable outcome, and thus blocks of rows of indexed together.

The row index includes a map from clustering keys or prefixes to the data position at the start of the index block which is the earliest that could contain a key equal or greater than the given one. Additionally, if there is an active deletion at the beginning of the block, the index must specify it so that it can be taken into account when merging data from multiple data files.

Each index block contains at least one key, or may include different first and last keys. The row trie index 220 indexes the positions between blocks by storing a "separator," a key that is greater than the last key of the previous block and smaller than or equal to the first key of the next. Then, a given clustering is looked up, following its bytes as long as we can in the trie. As such, all blocks before the closest less-than-or-equal entry in the trie cannot contain any data that is greater than or equal to the given key.

If the identified block actually doesn't contain any matching data (e.g. because the looked-up key ends up between the last key in the block and the separator), this only affects efficiency as the iteration mechanism does not expect the data position returned by the index to be guaranteed to start with elements that fit the criteria; it would only have to walk a whole block forward to find the matching key.

The number of these false positives should be kept low, and at the same time the smallest possible size of the index for a given granularity is desirable. The choice of separator affects this balance. In one example, as a good tradeoff in the vein of the unique prefix approach used in the partition index, the shortest prefix of the next block's beginning key that separates it from the previous block's end key is used, and adjusted so that the last byte of it is 1 greater than that end key.

For example, if block 2 covers "something" to "somewhere" and a next block 3 covers "sorry" to "tease", then the sequence "son" is used as the separator between blocks 2 and 3. This leaves things like "sommelier" in the area that triggers false positives, but stores and has to walk just three bytes to find the starting point for iteration.

Example Trie Index Application

Figure 4:
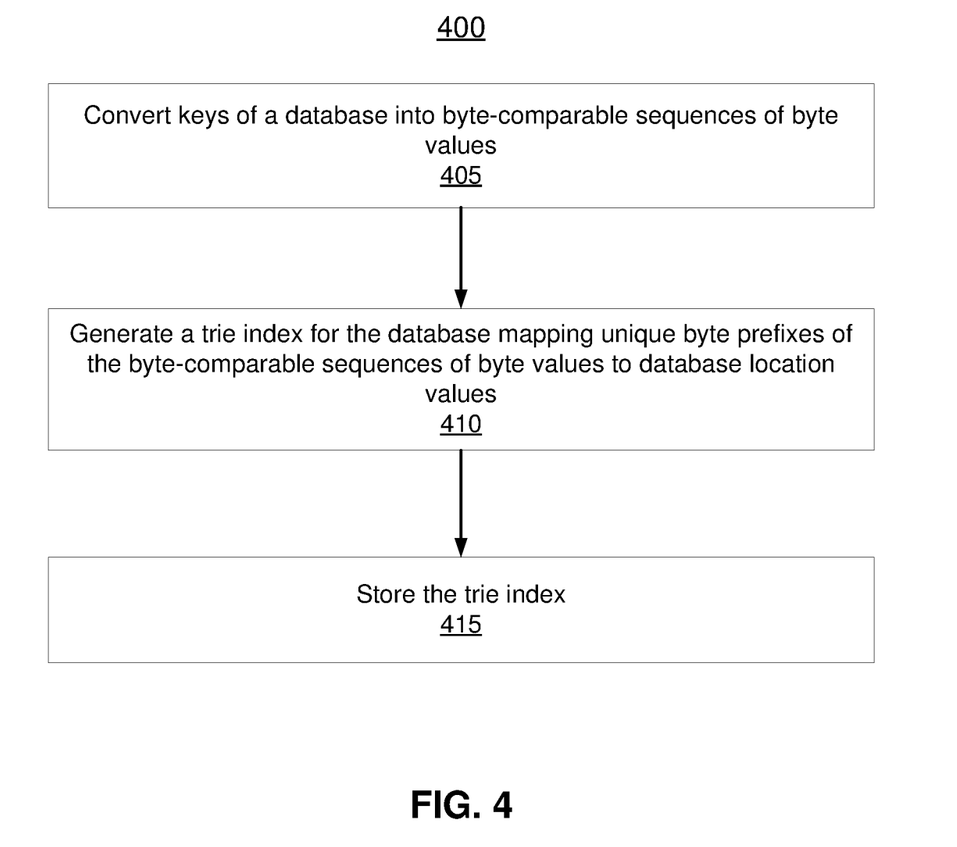
FIG. 4 is a flow chart of a process for generating a trie index for blocks of records, in accordance with some embodiments.

FIG. 4 is a flow chart of a process 400 for generating a trie index, in accordance with some embodiments. The process 400 provides for an indexing of a database using a trie index. The process 400 may include additional or fewer steps, and steps may be performed in different orders.

A database system (e.g., processor 104 of the system 100) converts 405 keys of a database into byte-comparable sequences of byte values. A key references a record stored in a row 116 of the database 110. The key may include data of multiple data types. Each of the data types is converted to a byte-comparable byte value to generate a byte-comparable sequence of bytes for the key. In some embodiments, each key of a database system such as Cassandra is converted into the byte-comparable sequences of byte values.

The database system generates 410 a trie index for the database mapping unique byte prefixes of the byte-comparable sequences of byte values to database location values. Each of the byte-comparable sequence of bytes has a unique byte prefix. The unique byte prefix of a byte-comparable sequence of bytes may include a minimum amount of byte values needed to distinguish the byte-comparable sequence of bytes from other byte-comparable sequences of bytes of the trie index. In some embodiments, the trie index uses the full byte-comparable sequences of byte values rather the unique byte prefixes. A database location value may refer to a position in a data file, a further level of indexing (e.g., referencing a row index), or other relevant information such as filtering hash bits, tombstone/deletion information, latest timestamp, or other metadata. The database location value may be different depending on whether the trie index is a partition index or row index.

The database system stores 415 the trie index. Nodes of the trie index may be stored in a memory as they are written, and periodically flushed to disk pages for more permanent storage. The manner in which the trie index is incorporated into the disk pages can improve efficiency of data access. To minimize transitions between different disk pages 324 when traversing the trie index 300, the trie index 300 may be distributed across multiple disk pages 324 with wide sections of the trie index 300 packed in each disk page 324 as shown in FIG. 3B. The trie index 300 may be stored across disk pages 324 using a bottom-up or top-down process. In some embodiments, the trie may be stored on disk in a page-packed manner, i.e. where the trie is written from the bottom up, delaying writes to disk until a branch becomes the biggest that can fit a disk page. The bottom-up process provides for incremental construction of the trie index.

In some embodiments, the trie index is stored with the smallest representation of each node. Examples of node types include PAYLOAD_ONLY (final), SINGLE, SPARSE, or DENSE. Node types define the size of each pointer of the node, or the number of children of the node in the trie index. Different node types are represented by different numbers of bytes, and thus smaller node types may be used when possible. The trie index 300 is stored in manner to minimize disk usage, and thus reduces cache usage and disk reads.

In some embodiments, the pointers in the nodes of the trie index are encoded using differences between a current and target position within the file.

Figure 5:
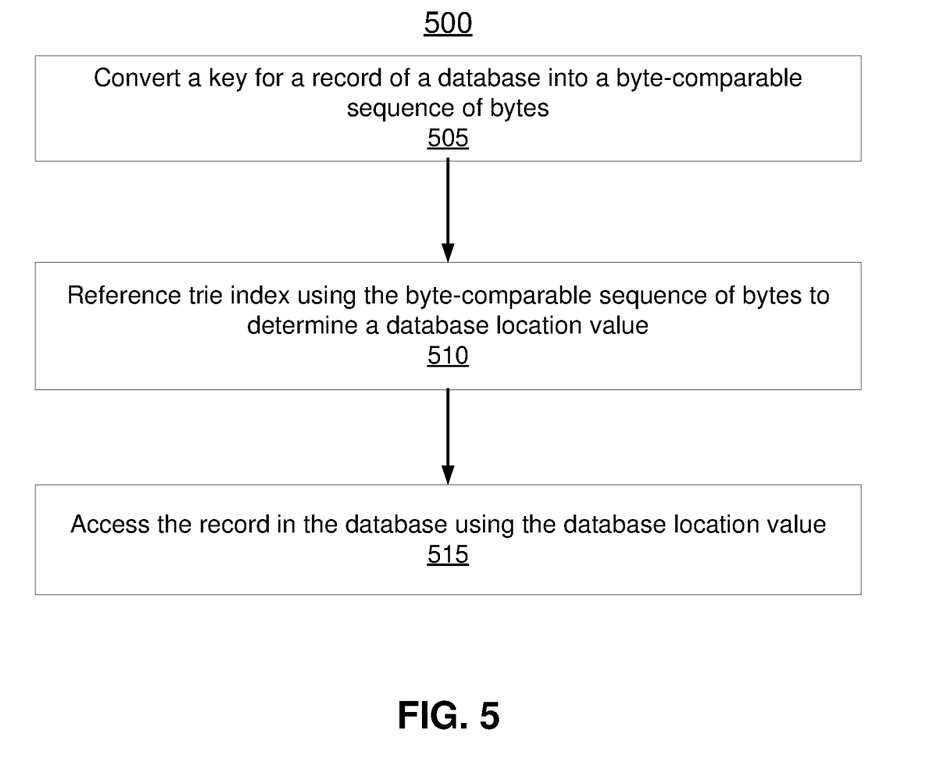
FIG. 5 is a flow chart of a process for accessing a record using a trie index, in accordance with some embodiments.

FIG. 5 is a flow chart of a process 500 for accessing a record using a trie index, in accordance with some embodiments. The process 500 may be performed to search for a record using the trie index, such as for read or write operations. The process 500 may include additional or fewer steps, and steps may be performed in different orders.

A database system (e.g., processor 104 of the system 100) converts 505 a key for a record of a database into a byte-comparable sequence of bytes. For example, the database system may receive query including the key. The key may include data of multiple data types. Each of the data types is converted to a byte-comparable byte value to generate a byte-comparable sequence of bytes for the key. In some embodiments, the key may be a primary key including a partition key used to reference a partition index, and a clustering key used to reference a row index.

The database system references 510 the trie index using the byte-comparable sequence of bytes to determine a database location value for the record. For example, the trie index 300 may be traversed from the root node 306 along edges 304. Each edge 304 may correspond with one or more byte values, and thus the byte-comparable sequence of bytes or a corresponding unique byte prefix defines a path along one or more edges 304. If a leaf node 308 with payload 310 is reached by traversing the trie index, the database location value is retrieved from the payload 310.

The database system accesses 515 the record in the database using the database location value. If the trie index is a partition index, the trie index maps byte-comparable sequences of bytes generated from partition keys to a position in a row index file (e.g., if the partition has enough rows to form multiple row index blocks), or directly to a position in a data file (e.g., if the partition has fewer rows). There may be one row index per partition, or no row index if the number of rows in the partition is below a row block size. The row index file contains a collection of trie row indices mapping row blocks to a position in the data file, and other relevant metadata.

Figure 6:
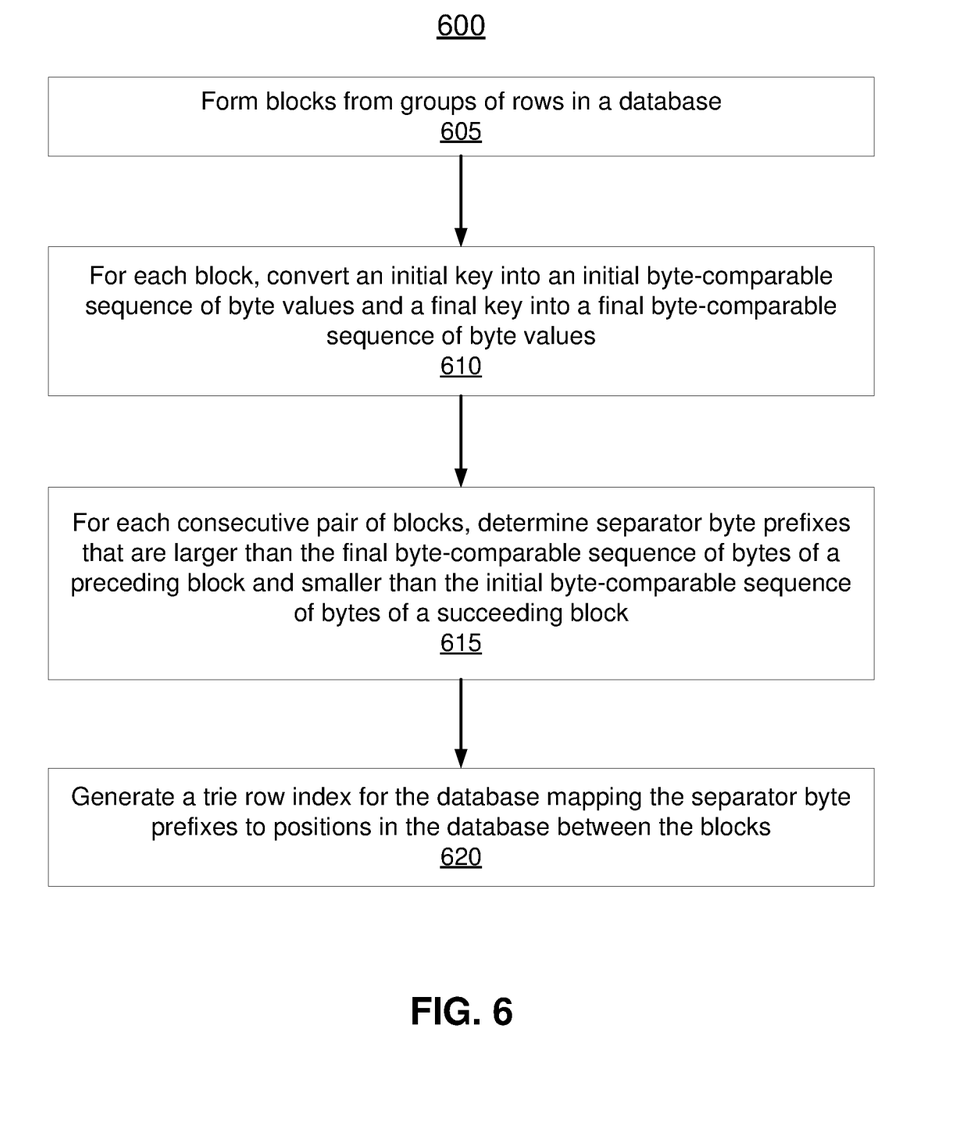
FIG. 6 is a flow chart of a process for generating a trie row index, in accordance with some embodiments.

FIG. 6 is a flow chart of a process 600 for generating a trie row index, in accordance with some embodiments. The process 600 may include additional or fewer steps, and steps may be performed in different orders.

The database system (e.g., processor 104 of the system 100) forms 605 blocks from groups of rows in a database. Each row in the database 110 may correspond with a record. The rows 116 of the database 110 may be small, and thus blocks of rows may be indexed together. The rows may be part of a partition.

For each block, the database system converts 610 an initial key into an initial byte-comparable sequence of bytes and a final key into a final byte-comparable sequence of bytes. Each row of the block is associated with a key. The initial key refers to the key of the first row in the block, and the final key refers to the key of the final row in the block.

For each consecutive pair of blocks, the database system determines 615 separator byte prefixes that are larger than the final byte-comparable sequence of bytes of a preceding block and smaller than the initial byte-comparable sequence of bytes of a succeeding block. Each pair of blocks includes a preceding and succeeding block.

The database system generates 620 a trie row index for the database mapping the separator byte prefixes to positions in the database between the blocks. For example, the trie row index associates the separator byte prefix for each pair of preceding and succeeding blocks to a position in the database (e.g., a data file) between the preceding and the succeeding block. The trie row index may include nodes connected by edges, with each edge being associated with a byte value. The separator byte prefixes are defined by paths from root node to a leaf node in the trie row index along edges, and the position in the database for a separator byte prefix is stored at the leaf node of the path.

The database system stores 625 the trie row index. The trie row index may be stored across disk pages 324 using a top-down or bottom-up process. The trie index may also be stored with the smallest representation of each node using node types represented by different numbers of bytes.

Figure 7:
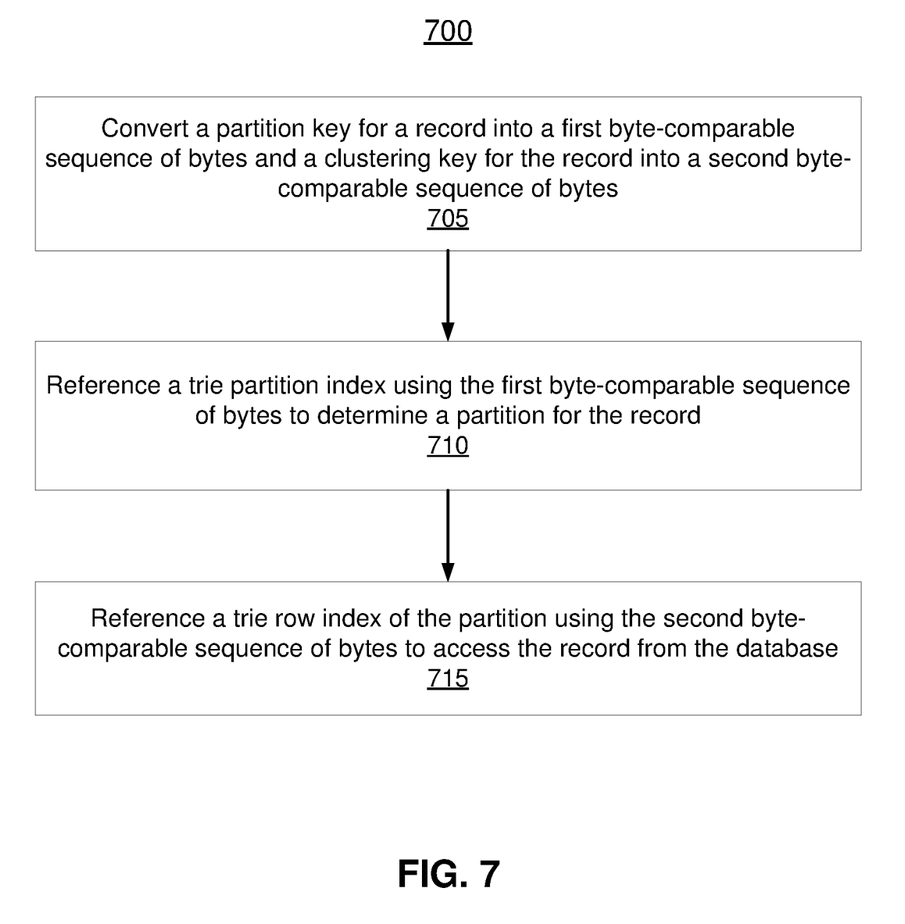
FIG. 7 is a flow chart of a process for accessing a record using a trie partition index and a trie row index, in accordance with some embodiments.

FIG. 7 is a flow chart of a process 700 for accessing a record using a trie partition index and a trie row index, in accordance with some embodiments. The process 700 may include additional or fewer steps, and steps may be performed in different orders.

A database system (e.g., processor 104 of the system 100) converts 705 a partition key into a first byte-comparable sequence of bytes and a clustering key into a second byte-comparable sequence of bytes. A key for a record in a database may be a primary key including the partition key that is used to reference the trie partition index 212 to identify a partition, and the clustering key that is used to reference a row trie index 220 to identify a row within the partition. For example, the database system may receive query including the primary key. The primary key may include data of multiple data types. Each of the data types is converted to a byte-comparable byte value to generate the byte-comparable sequence of bytes for the key. The byte-comparable sequence of bytes may include the first sequence of bytes for the partition key and the second sequence of bytes for the clustering key.

The database system references 710 the trie partition index using the first byte-comparable sequence of bytes of the partition key to determine a partition for the record. For example, the partition trie index 212 may be traversed from the root node along edges according to the bytes of the partition key. Each edge may correspond with one or more byte values, and thus the byte-comparable sequence of bytes of the partition key, or a corresponding unique byte prefix of the byte-comparable sequence of bytes, defines a path along one or more edges. If a leaf node with payload is reached by traversing the trie index, a database location value is retrieved from the payload 310. Here, the database location value identifies the partition and the associated trie row index of the partition. For example, the database location may include location in a row index file that includes the trie row index associated with the partition.

The database system references 715 a trie row index of the partition using the second byte-comparable sequence of bytes to access the record. For example, the database location value retrieved from referencing the partition trie index 212 is used to retrieve the trie row index. The partition index may map the first byte-comparable sequences of bytes generated from the converted partition key to a position in a row index file that stores the trie row index. Next, there is an iteration using the clustering key in forward or reverse direction through the trie row index.

Figure 8:
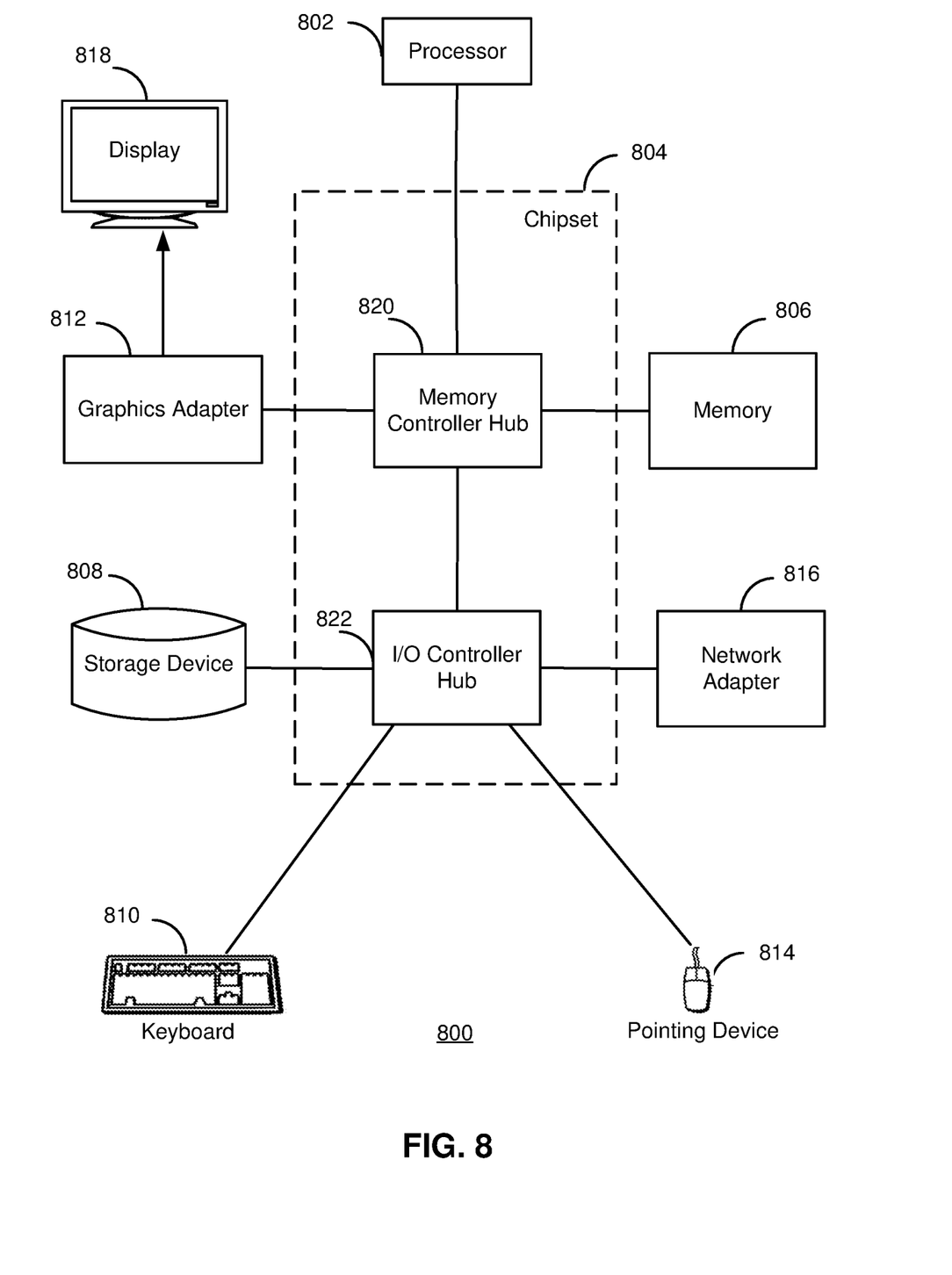
FIG. 8 is a schematic block diagram of a computer used in the database system, in accordance with some embodiments.

FIG. 8 is a schematic block diagram of a computer 800, according to one embodiment. The computer 800 is an example of circuitry that implements components of the database system 100. Illustrated are at least one processor 802 coupled to a chipset 804. The chipset 804 includes a memory controller hub 820 and an input/output (I/O) controller hub 822. A memory 806 and a graphics adapter 812 are coupled to the memory controller hub 820, and a display device 818 is coupled to the graphics adapter 812. A storage device 808, keyboard 810, pointing device 814, and network adapter 816 are coupled to the I/O controller hub 822. Other embodiments of the computer 800 have different architectures. For example, the memory 806 is directly coupled to the processor 802 in some embodiments.

The storage device 808 includes one or more non-transitory computer-readable storage media such as a hard drive, compact disk read-only memory (CD-ROM), DVD, or a solid-state memory device. The memory 806 holds instructions and data used by the processor 802. The pointing device 814 is used in combination with the keyboard 810 to input data into the computer system 800. The graphics adapter 812 displays images and other information on the display device 818. In some embodiments, the display device 818 includes a touch screen capability for receiving user input and selections. The network adapter 816 couples the computer system 800 to a network. Some embodiments of the computer 800 have different and/or other components than those shown in FIG. 8.

The computer 800 is adapted to execute computer program modules for providing functionality described herein. For example, some embodiments may include a computing device including one or more modules configured to perform the processes 400, 500, 600, and 700 shown respectively in FIGS. 4, 5, 6, and 7. As used herein, the term "module" refers to computer program instructions and/or other logic used to provide the specified functionality. Thus, a module can be implemented in hardware, firmware, and/or software. In one embodiment, program modules formed of executable computer program instructions are stored on the storage device 808, loaded into the memory 806, and executed by the processor 802.

While particular embodiments and applications have been illustrated and described, it is to be understood that the invention is not limited to the precise construction and components disclosed herein and that various modifications, changes and variations which will be apparent to those skilled in the art may be made in the arrangement, operation and details of the method and apparatus disclosed herein without departing from the spirit and scope of the present disclosure.

What is claimed is:

1. A database system, comprising:
a cluster of database nodes that stores a distributed database, each database node storing one or more partitions of the distributed database, each partition including a set of database rows, each database node including:
one or more processors; and
a memory storing instructions that, when executed by the one or more processors, cause the one or more processors to:
access a key for a record including a partition key and a clustering key;
convert the key into a byte-comparable sequence of byte values comprising a first portion of the byte-comparable sequence of bytes obtained from the partition key and a second portion of the byte-comparable sequence of bytes obtained from the clustering key;
reference a partition trie index using the byte-comparable sequence of byte values of the record generated from the key to determine a partition of the distributed database; and
access the record from the partition of the distributed database.

2. The database system of claim 1, wherein the instructions when executed by the one or more processors, cause the one or more processors to:
access the partition trie index using the first portion of the byte-comparable sequence.

3. The database system of claim 1, wherein the instructions when executed by the one or more processors, cause the one or more processors to:
access a row trie index using the second portion of the byte-comparable sequence.

4. The database system of claim 3, wherein the partition trie index and the row trie index provide an index of records stored in the rows and columns of a partition.

5. The database system of claim 3, wherein the partition trie index and the row trie index each comprise a trie data structure that describes a mapping between sequences of byte values and database location values of the database.

6. The database system of claim 3, wherein the partition trie index maps to database location values of the row trie index.

7. The database system of claim 6, wherein the row trie index maps to database location values of the rows.

8. A non-transitory computer readable memory storing instructions that, when executed by one or more processors, cause the one or more processors to:
store a distributed database in a cluster of database nodes, each database node storing one or more partitions of the distributed database, each partition including a set of database rows, each database node including:
access a key for a record including a partition key and a clustering key;
convert the key into a byte-comparable sequence of byte values comprising a first portion of the byte-comparable sequence of bytes obtained from the partition key and a second portion of the byte-comparable sequence of bytes obtained from the clustering key;
reference a partition trie index using the byte-comparable sequence of byte values of the record generated from the key to determine a partition of the distributed database; and
access the record from the partition of the distributed database.

9. The computer readable memory of claim 8, wherein the instructions when executed by the one or more processors, cause the one or more processors to:
access a partition trie index using the first portion of the byte-comparable sequence.

10. The computer readable memory of claim 8, wherein the instructions when executed by the one or more processors, cause the one or more processors to:
access a row trie index using the second portion of the byte-comparable sequence.

11. The computer readable memory of claim 10, wherein the partition trie index and the row trie index provide an index of records stored in the rows and columns of a partition.

12. The computer readable memory of claim 10, wherein the partition trie index and the row trie index each comprise a trie data structure that describes a mapping between sequences of byte values and database location values of the database.

13. The computer readable memory of claim 10, wherein the partition trie index maps to database location values of the row trie index.

14. The computer readable memory of claim 13, wherein the row trie index maps to database location values of the rows.

15. A method, comprising:
   storing a distributed database in a cluster of database nodes, each database node storing one or more partitions of the distributed database, each partition including a set of database rows, each database node including:
   accessing a key for a record including a partition key and a clustering key;
   converting the key into a byte-comparable sequence of byte values comprising a first portion of the byte-comparable sequence of bytes obtained from the partition key and a second portion of the byte-comparable sequence of bytes obtained from the clustering key;
   referencing a partition trie index using the byte-comparable sequence of byte values of the record generated from the key to determine a partition of the distributed database; and
   accessing the record from the partition of the distributed database.

16. The method of claim 15, further comprising:
   accessing a partition trie index using the first portion of the byte-comparable sequence.

17. The method of claim 15, further comprising:
   accessing a row trie index using the second portion of the byte-comparable sequence.

18. The method of claim 17, wherein the partition trie index and row trie index provide an index of records stored in the rows and columns of a partition.

19. The method of claim 17, wherein the partition trie index and the row trie index each comprise a trie data structure that describes a mapping between sequences of byte values and database location values of the database.

20. The method of claim 17, wherein the partition trie index maps to database location values of the row trie index and the row trie index maps to database location values of the rows.

* * * * *

UNITED STATES PATENT AND TRADEMARK OFFICE
CERTIFICATE OF CORRECTION

PATENT NO. : 11,899,641 B2
APPLICATION NO. : 17/549570
DATED : February 13, 2024
INVENTOR(S) : Branimir Zdravkov Lambov Page 1 of 1

It is certified that error appears in the above-identified patent and that said Letters Patent is hereby corrected as shown below:

In the Claims

In Column 14, in Claim 9, Line 58, before "computer" insert -- non-transitory --.

In Column 14, in Claim 10, Line 63, before "computer" insert -- non-transitory --.

In Column 15, in Claim 11, Line 1, before "computer" insert -- non-transitory --.

In Column 15, in Claim 12, Line 5, before "computer" insert -- non-transitory --.

In Column 15, in Claim 13, Line 10, before "computer" insert -- non-transitory --.

In Column 15, in Claim 14, Line 13, before "computer" insert -- non-transitory --.

Signed and Sealed this
Twenty-fifth Day of March, 2025

Coke Morgan Stewart
*Acting Director of the United States Patent and Trademark Office*